United States Patent
Wu et al.

(10) Patent No.: US 11,254,709 B2
(45) Date of Patent: Feb. 22, 2022

(54) **METHOD FOR PROMOTING *BACILLUS SUBTILIS* TO SYNTHESIZE SURFACTIN BASED ON MULTI-GENE SYNERGY**

(71) Applicant: Jiangnan University, Wuxi (CN)

(72) Inventors: Qun Wu, Wuxi (CN); Yan Xu, Wuxi (CN)

(73) Assignee: Jiangnan University, Wuxi (CN)

( * ) Notice: Subject to any disclaimer, the term of this patent is extended or adjusted under 35 U.S.C. 154(b) by 486 days.

(21) Appl. No.: 16/220,019

(22) Filed: Dec. 14, 2018

(65) Prior Publication Data

US 2020/0131229 A1    Apr. 30, 2020

(51) Int. Cl.

| | |
|---|---|
| *C12N 15/67* | (2006.01) |
| *C07K 7/64* | (2006.01) |
| *C07K 14/32* | (2006.01) |
| *C12N 15/52* | (2006.01) |
| *C12N 15/75* | (2006.01) |
| *C12N 1/20* | (2006.01) |
| *C12R 1/125* | (2006.01) |

(52) U.S. Cl.
CPC .............. *C07K 7/64* (2013.01); *C07K 14/32* (2013.01); *C12N 1/20* (2013.01); *C12N 1/205* (2021.05); *C12N 15/52* (2013.01); *C12N 15/67* (2013.01); *C12N 15/75* (2013.01); *C12R 2001/125* (2021.05)

(58) Field of Classification Search
None
See application file for complete search history.

(56) References Cited

PUBLICATIONS

Dhali et al. 2017 (Genetic engineering of the branched fatty acid metabolic pathway of Bacillus subtilis for the overproduction of surfactin C14 isoform; Biotechnol. J 12: 1600574 (Year: 2017).*

Kinsinger et al. 2005 (Genetic requirements for potassium ion-dependent colony spreading in Bacillus subtilis; Journal of Bacteriology 187(24): 8462-8469) (Year: 2005).*

Wang et al., 2019 (Enhancing surfactin production by using systematic CRISPRi repression to screen amino acid biosynthesis genes in Bacillus subtilis; Microbil Cell Factories 18:90 (Year: 2019).*

Wu et al., 2019 (Systematically engineering the biosynthesis of a green biosurfactant surfactin by Bacillus subtilis 168; Metabolic Engineering 52: 87-97); (Year: 2019).*

* cited by examiner

*Primary Examiner* — Mary Maille Lyons
(74) *Attorney, Agent, or Firm* — IPro, PLLC

(57) ABSTRACT

The present invention discloses a method for promoting *B. subtilis* to synthesize surfactin based on multi-gene synergy, and belongs to the field of genetic engineering. Firstly, *B. subtilis* is enabled to obtain the ability to synthesize surfactin by integrant expression of sfp protein derived from a high-yield strain, on this basis, by knocking out genes associated with a competitive pathway, overexpressing genes associated with the surfactin tolerance of *B. subtilis*, strengthening genes associated with a branched chain fatty acid synthesis pathway or improving the intracellular srfA gene transcription level, the synergy among genes is realized, and systemic metabolic engineering transformation is performed on the *B. subtilis*, thereby greatly improving the ability of *B. subtilis* genetically engineered bacteria to synthesize surfactin. Compared with a starting strain *B. subtilis* 168, the amount of extracellular accumulation of surfactin of the *B. subtilis* genetically engineered bacteria increases from 0 g/L to 12.8 g/L. The present invention obtains the recombinant *B. subtilis* with significantly improved ability to synthesize surfactin by multi-gene cooperative transformation of *B. subtilis*, and has a good application prospect.

12 Claims, No Drawings

Specification includes a Sequence Listing.

METHOD FOR PROMOTING *BACILLUS SUBTILIS* TO SYNTHESIZE SURFACTIN BASED ON MULTI-GENE SYNERGY

TECHNICAL FIELD

The disclosure herein relates to a method for promoting *Bacillus subtilis* to synthesize surfactin based on multi-gene synergy, and belongs to the field of genetic engineering.

BACKGROUND

Surfactin is a cyclo-heptapeptide compound synthesized by *Bacillus* by non-ribosome peptide synthases (NRPS). Surfactin has unique biochemical activities, including significant surface activity, emulsification activity, and biological activities such as antibacterial, antiviral, anticancer and thrombolytic activities, and has extensive industrial application value in fields such as food, daily use, biopharmaceuticals, crude oil recovery and environmental remediation. At present, surfactin is mainly produced by transforming *Bacillus*, and the transformation methods are based on single gene or single pathway modification.

*B. subtilis* is a production host widely used as a food enzyme preparation and an important nutrient chemical. Its products are certified by the FDA as the security level of "generally regarded as safe" (GRAS). Wild type *B. subtilis* 168 does not have ability to synthesize surfactin. Therefore, how to realize the synthesis of surfactin and improve the synthesis ability of *B. subtilis* 168 is an urgent problem to be solved to improve the yield of the surfactin.

SUMMARY

In order to solve the above problems, the present invention provides a method for improving the ability of *B. subtilis* to synthesize surfactin and recombinant *B. subtilis* with high yield of surfactin.

The first aim of the present invention is to provide the method for improving the ability of *B. subtilis* to synthesize surfactin, and the method comprises the following steps: replacing an original sfp genes of *B. subtilis* with other sfp genes capable of complete expression to enable recombinant bacteria to express complete Sfp protein; and performing transformations as follows: knocking out at least one of gene clusters associated with biofilm formation, NRPS/PKS gene clusters or genes associated with negative regulatory factors, and/or, overexpressing at least one of surfactin efflux and resistance genes, genes associated with a branched chain fatty acid synthesis pathway, genes associated with a glycolytic pathway, and a gene associated with an exogenous cluster effect system.

In one example of the present invention, the original sfp genes are replaced with sfp genes derived from *Bacillus amyloliquefaciens* by the method.

In one example of the present invention, starting from *B. subtilis* 168, the original sfp genes of *B. subtilis* 168 are replaced with sfp genes derived from *B. amyloliquefaciens* MT45 by homologous recombination. The *B. amyloliquefaciens* MT45 has been preserved in China General Microbiological Culture Collection Center with the preservation number of CGMCC: 12593, and published in 2017 in a publication entitled "Genome and transcriptome analysis of surfactin biosynthesis in *Bacillus amyloliquefaciens* MT45".

In one example of the present invention, the gene clusters associated with biofilm formation comprise epsA-O and tasA-sipW-yqxM; the NRPS/PKS gene clusters comprise dhb operon expressing a siderophore bacillibactin synthase, pks operon expressing an unknown polyketide synthase, and pps operon expressing a fengycin synthase; the genes associated with the negative regulatory factors comprise codY, rapCFH, sinI, spx, perR and phoP.

In one example of the present invention, the surfactin efflux and resistance genes comprise swrC, liaRSFGHI and acrB; the genes associated with the branched chain fatty acid synthesis pathway comprise fabHB, IpdV, bkdAA, bkdAB, bkdB, lipALM, alsS, ilvD, ilvC, leuABCD, fabD, accD-ABC, fabF, fabG, fabZ, fabI and tesA; the genes associated with the glycolytic pathway comprise pfkA, gapA, pgk and pdhABCD; the gene associated with the exogenous cluster effect system comprises comQXPA.

In one example of the present invention, at least two genes of the gene clusters associated with biofilm formation, the NRPS/PKS gene clusters or the genes associated with the negative regulatory factors are knocked out.

In one example of the present invention, at least two genes of the surfactin efflux and resistance genes, the genes associated with the branched chain fatty acid synthesis pathway, the genes associated with the glycolytic pathway, and the gene associated with the exogenous cluster effect system are overexpressed.

In one example of the present invention, at least one gene of the gene clusters associated with biofilm formation, the NRPS/PKS gene clusters or the genes associated with the negative regulatory factors is knocked out, and at least one gene of the surfactin efflux and resistance genes, the genes associated with the branched chain fatty acid synthesis pathway, the genes associated with the glycolytic pathway, and the gene associated with the exogenous cluster effect system is overexpressed; the gene clusters associated with biofilm formation comprise epsA-O and tasA-sipW-yqxM; the NRPS/PKS gene clusters comprise dhb operon expressing a siderophore bacillibactin synthase, pks operon expressing an unknown polyketide synthase, and pps operon expressing a fengycin synthase; the genes associated with the negative regulatory factors comprise codY, rapCFH, sinI, spx, perR and phoP; the surfactin efflux and resistance genes comprise swrC, liaRSFGHI and acrB; the genes associated with the branched chain fatty acid synthesis pathway comprise fabHB, IpdV, bkdAA, bkdAB bkdB, lipALM, alsS, ilvD, ilvC, leuABCD, fabD-accDABC, fabF-fabG-fabZ-fabI and tesA; the genes associated with the glycolytic pathway comprise pfkA, gapA, pgk and pdhABCD; the gene associated with the exogenous cluster effect system comprises comQXPA.

In one example of the present invention, overexpression is performed by a P43 promoter.

In one example of the present invention, the comQXPA and srfA promoters are combined for expression.

In one example of the present invention, the knockout is performed by a homologous recombination knockout method, and the length of a homologous arm used for knockout is 1000-2000 bp.

In one example of the present invention, the knockout is performed by a method of traceless knockout.

In one example of the present invention, fusion of multiple gene fragments is performed by using a two-step approach.

In one example of the present invention, the recombinant *B. subtilis* is prepared by replacing the sfp genes in *B. subtilis* 168 with sfp genes derived from *B. amyloliquefaciens* MT45, knocking out epsA-O, tasA-sipW-yqxM, dhb operon, pks operon, pps operon, codY, rapCFH, sinI, spx, perR and phoP genes, and overexpressing fabHB, IpdV, bkdAA, bkdAB, bkdB, lipALM, alsS, ilvD, ilvC, leuABCD, fabD-accDABC, fabF-fabG-fabZ-fabI, tesA, pfkA, gapA, pgk, pdhABCD and comQXPA genes.

In one example of the present invention, the position of the dhb operon on genome of *B. subtilis* 168 (GenBank accession number: CP019663.1) is 3279963-3292268; the position of the pks operon on genome of *B. subtilis* (GenBank accession number: CP019663.1) is 1781529-1859801; the position of the pps operon on genome of *B. subtilis* 168 (GenBank accession number: CP019663.1) is 1959874-1998127; the Gene ID of the codY on NCBI is 936491; the Gene IDs of the rapCFH on NCBI are 938284, 936725 and 936065 (respectively corresponding to rapC, rapF and rapH); the Gene ID of the sinI on NCBI is 938543; the GenBank accession number of the spx on NCBI is AQR81102.1; the Gene ID of the perR on NCBI is 939227; the Gene ID of the phoP on NCBI is 936644; the GenBank accession number of the swrC on NCBI is ASF27968.1; the Gene IDs of the liaRSFGHI on NCBI are 935957, 935967, 938469, 938471, 938585 and 935958; the GenBank accession number of the acrB on NCBI is ASF27461.1; the Gene IDs of the fabHB and IpdV on NCBI are respectively 939306 and 938669; the Gene ID of bkdAA on NCBI is 938674; the Gene ID of bkdAB on NCBI is 938672; the Gene ID of bkdB on NCBI is 938677; the Gene IDs of lipALM on NCBI are 938861, 937083 and 938551; the Gene IDs of ilvD and ilvC on NCBI are 939084 and 937475; the Gene IDs of leuABCD on NCBI are 936316, 936221, 937478 and 937683; the Gene ID of fabD on NCBI is 938488; the Gene IDs of accDABC on NCBI are 936186, 936367, 938587 and 938588; the Gene IDs of fabF, fabG, fabZ and fabI on NCBI are 939803, 938113, 936918 and 939379; the Gene ID of tesA on NCBI is 938545; the Gene ID of pfkA on NCBI is 937376; the Gene ID of gapA on NCBI is 938627; the Gene ID of pgk on NCBI is 938572; the Gene IDs of pdhABCD on NCBI are 936005, 939496, 936010 and 939492; the Gene IDs of comQXPA on NCBI are 937180, 938875, 938866 and 937179.

The second aim of the present invention is to provide recombinant *B. subtilis* for synthesizing surfactin. On the basis of integrant expression of Sfp protein derived from *B. amyloliquefaciens* MT45, the method performs transformations as follows: knocking out at least one of the gene clusters associated with biofilm formation, the NRPS/PKS gene clusters or the genes associated with the negative regulatory factors, and/or, overexpressing surfactin efflux and resistance genes, genes associated with a branched chain fatty acid synthesis pathway, genes associated with a glycolytic pathway, and a gene associated with an exogenous cluster effect system.

In one example of the present invention, the gene clusters associated with biofilm formation comprise epsA-O and tasA-sipW-yqxM; the NRPS/PKS gene clusters comprise dhb operon expressing a siderophore bacillibactin synthase, pks operon expressing an unknown polyketide synthase, and pps operon expressing a fengycin synthase; the genes associated with the negative regulatory factors comprise codY, rapCFH, sinI, spx, perR and phoP.

In one example of the present invention, the surfactin efflux and resistance genes comprise swrC, liaRSFGHI and acrB; the genes associated with the branched chain fatty acid synthesis pathway comprise fabHB, IpdV, bkdAA, bkdAB, bkdB, lipALM, aisS ilvD, ilvC, leuABCD, fabD-accDABC, fabF-fabG-fabZ-fabI and tesA; the genes associated with the glycolytic pathway comprise pfkA, gapA, pgk and pdhABCD; the gene associated with the exogenous cluster effect system comprises comQXPA.

In one example of the present invention, overexpression is performed by a P43 promoter.

The third aim of the present invention is to provide a method for promoting *B. subtilis* to synthesize surfactin, which is characterized by realizing fermentation production of surfactin with the recombinant *B. subtilis* as a production strain.

In one example of the present invention, a fermentation medium used for fermentation contains 60-65 g/L of sucrose, 5-10 g/L of ammonium nitrate, 3-5 g/L of peptone, 2-5 g/L of potassium dihydrogen phosphate, 8-12 g/L of disodium hydrogen phosphate, 0.05-0.15 g/L of magnesium sulfate, 5-8 μM of calcium chloride, 2-5 μM of ferrous sulfate and 2-5 μM of EDTA.

In one example of the present invention, the fermentation medium used for fermentation contains 65 g/L of sucrose, 8 g/L of ammonium nitrate, 3.73 g/L of peptone, 4.08 g/L of potassium dihydrogen phosphate, 10 g/L of disodium hydrogen phosphate, 0.096 g/L of magnesium sulfate, 7 μM of calcium chloride, 4 μM of ferrous sulfate and 4 μM of EDTA.

In one example of the present invention, fermentation is performed by activating the production strain, transferring the strain to 50 mL of the fermentation medium according to inoculum size of 2%, and in a 250 mL triangular flask serving as a container, at pH 7.0 and 30° C., performing shake culture at 200 rpm for 60 h.

The present invention also claims a product containing surfactin produced by fermentation of the strain.

Advantageous Effects of the Invention: Firstly, the ability to synthesize surfactin is obtained by integrant expression of Sfp protein derived from a high-yield strain, on this basis, by knocking out a competitive pathway, overexpressing surfactin self-tolerance genes, strengthening the branched chain fatty acid synthesis pathway or improving the intracellular srfA gene transcription level, the synergy among genes is realized, and systemic metabolic engineering transformation is performed on the starting strain, thereby greatly improving the ability of the engineering bacteria to synthesize surfactin. The recombinant *B. subtilis* S35 of the present invention is prepared by replacing the sfp genes with sfp genes derived from *B. amyloliquefaciens* MT45 on the basis of *B. subtilis* 168, knocking out epsA-O, tasA-sipW-yqxM, dhb operon, pks operon, pps operon, codY genes, and overexpressing fabHB, IpdV bkdAA bkdAB bkdB, lipALM, alsS ilvD ilvC leuABCD, fabD-accDABC, fabF-fabG-fabZ-fabI, tesA, pfkA, gapA, pgk, pdhABCD and comQXPA genes and PsrfA.

Compared with the starting strain 168, the amount of extracellular accumulation of surfactin increases from 0 g/L to a concentration of 12.8 g/L. The multi-gene cooperative recombinant *B. subtilis* construction method of the present invention effectively improves the yield of surfactin, is convenient to use, and has a good application prospect.

DETAILED DESCRIPTION

Method for determination of surfactin: performing detection by ultra-performance liquid chromatography (UPLC), specifically comprises Agilent, H-Class, UV-detector; Waters BEH C18 chromatographic column: 100 mm*2.1 mm, 1.7 μm particle; UV detection wavelength: 205 nm; mobile phases: A is 0.1% aqueous formic acid, and mobile phase B is HPLC grade methanol; elution gradient: 0.1 min, 70% B; 0.1-2.0 min, 70% B; 2.0-8.0 min, 70%-100% B; 8.0-10 min, 100% B; 10.1 min, 70% B, 10.1-13 min 70% B; flow rate: 0.3 ml/min.

Seed medium (g/L): 10 of tryptone, 5 of yeast powder and 10 of NaCl.

Fermentation medium (g/L) (synthetic medium): 65 of sucrose, 8 of ammonium nitrate, 3.73 of peptone, 4.08 of potassium dihydrogen phosphate, 10 of disodium hydrogen phosphate, 0.096 of magnesium sulfate, 7 μM of calcium chloride, 4 μM of ferrous sulfate and 4 μM of EDTA.

Culture condition: transferring a seed cultured at 30° C. at 220 rpm for 10 h to 50 mL of the fermentation medium according to inoculum size of 2%, and in a 250 mL triangular flask as a container, at pH7.0 and 30° C., performing shake culture at 200 rpm for 60 h.

TABLE 1

| Primer | Primers Sequences (5'-3') | SEQ ID NO |
|---|---|---|
| D-1 | AATTGTTATTGATTTTATATGCTGC | 1 |
| D-2 | AATGTATGCTATACGAACGGTAATGGACCGTCTTT CTTTTCTAA | 2 |
| D-5 | AGCATACATTATACGAACGGTATTATTGATTTGCC AAAATGACA | 3 |
| D-6 | AAGTGCTGGAGCCGGGAGAAGAAAC | 4 |
| lox-F | TTAGAAAAGAAAGACGGTCCATTACCGTTCGTATA GCATACATT | 5 |
| lox-R | TGTCATTTTGGCAAATCAATAATACCGTTCGTATA ATGTATGCT | 6 |
| O-1 | ATGAACAAACATGTAAATAAAGTAG | 7 |
| O-2 | TGTATGCTATACGAACGGTAGAAACGGAATCTCGC AGAAT | 8 |
| O-5 | CATACATTATACGAACGGTACGCCGAAATGCCTCC GGTTT | 9 |
| O-6 | AAACATTGTTGAAGTTCATCATGTGTACATTCCTC TCTTACC | 10 |
| O-7 | GGTAAGAGAGGAATGTACACATGATGAACTTCAAC AATGTTT | 11 |
| O-8 | CCAAACAGGAAGCTCTGTGTCTTATGAGTCATGAT TTACTAA | 12 |
| O-9 | TTAGTAAATCATGACTCATAAGACACAGAGCTTCC TGTTTGG | 13 |
| O-10 | GTTGCGGTTAGTTGACTTTTTGTT | 14 |

Example 1: Construction and Traceless Knockout Method of B. subtilis Integrated Fragments (1) Construction of B. subtilis Knockout Integrated Fragments Taking pps genes as an example, a one-step fusion PCR method is used to perform three-fragment fusion to construct integrated fragments of the desired knockout genes. Firstly, according to the B. subtilis 168 genomic information published by NCBI, or by self-test of B. amyloliquefaciens MT45 genomic information, primers D-1/2 and D-5/6 are designed to respectively amplify the upstream and downstream homologous arm fragments of the target genes by using the genome of the target gene pps as a template, and fragments D-12 and D-56 are respectively obtained by gel recovery purification. In order to ensure homologous recombination efficiency, the lengths of the upstream and downstream homologous arm fragments are designed to be about 1000 bp. Plasmids p7S6, p7Z6 and p7E6 are used as templates to design primers lox-F/R to respectively amplify lox71-spc-lox66, lox71-zeo-lox66 and lox71-erm-lox66 antibiotic expression cassettes, and an antibiotic gene fragment numbered D-34 is obtained by gel recovery purification. Fragments D-12, D-34 and D-56 are used as templates mutually and mixed in a molar ratio of 1:1:1 (total amount not exceeding 500 ng), primers D-1/6 (0.5 μl each) and high-fidelity enzymes (25 μl) are added, and PCR amplification is performed according to the following procedure: 98° C., 30 s; 98° C., 10 s; 55° C., 10 s; 72° C., reaction time is the total fragment length/1000 min, 30 cycles. The resulting fragment directly transforms B. subtilis competent cells.

(2) Construction of B. subtilis Overexpressed Integrated Fragments

A two-step fusion PCR method is used to efficiently fuse multiple fragments to construct integrated fragments of the desired overexpressed genes. The specific process is shown in the figure. Taking the tesA gene as an example, primers O-1/2, lox-F/R, O-5/6, O-7/8 and O-9/10 are used respectively for amplification, and an upstream gene fragment O-12, a promoter fragment O-56, an overexpressed target gene fragment O-78, and a downstream homologous arm fragment O-910 are obtained by gel recovery purification. In the first step of fusion PCR, O-12, lox-F/R, D-34, O-56, O-78 and O-910 in an equimolar ratio are used as templates (total template amount not exceeding 50 ng), a strategy of low annealing temperature and long annealing time is used for performing fusion; a PCR procedure is as follows: 98° C., 1 min; 98° C., 30 s; 52.5° C., 2 min; 72° C., (fragment total length/1000) min, 15 cycles. In the second step of PCR, the fusion PCR product of the first step is used as a template to redesign a pair of nested PCR primers O-F/R, and a strategy of high annealing temperature and short annealing time is used for improving specific amplification of PCR; a PCR procedure is as follows: 98° C., 20 s; 98° C., 10 s; 55° C., 5 s; 72° C., (fragment length/1000, i.e. time counted by 1000 bp per minute) min, 30 cycles. The resulting fusion fragment directly transforms B. subtilis competent cells. The improved two-step fusion PCR strategy can achieve rapid and efficient fusion of multiple and long (greater than 15000 bp) fragments, which lays a foundation for later metabolic engineering transformation of strains.

(3) Traceless Elimination of Resistance Genes

Gene traceless elimination of Bacillus is performed by using a Cre-lox system. The screened target positive transformants carrying the resistance genes are recommenced and the competent state is prepared; plasmid pDR244 or pDG148-cre carrying Cre recombinase is transformed; screening is performed on a corresponding resistant tablet and transformants are verified by a colony PCR method; the obtained positive transformants subjected to the secondary transformation are cultured overnight in test tubes containing corresponding resistant LB, streaked to an LB nonresistant tablet, and cultured at 55° C. for 18 h or longer; PCR is performed on the obtained single colonies to verify whether the resistance genes are eliminated.

Example 2 Construction of B. subtilis Strain 168S1 with Integrant Expression of Sfp Genes Derived from B. amyloliquefaciens MT45

According to the same strategy as in Example 1, the complete sfp genes derived from B. amyloliquefaciens MT45 are integrated into the corresponding sites of B. subtilis 168 genome, the original inactive sfp genes of the strain 168 are replaced, and the ability of the strain 168 to synthesize surfactin is restored to obtain a recombinant strain 168S1. The yield of surfactin of the recombinant strain 168S1 is 0.4 g/L.

Example 3 Construction of Strain with epsA-O Gene Cluster and tasA-sipW-yqxM Operon Knocked Out On the basis of the recombinant strain 168S1, the recombinant strain 168S1 is subjected to traceless gene knockout by using the Cre-lox system according to the same strategy as in Example 1. At the same time, the epsA-O gene cluster and tasA-sipW-yqxM operon are knocked out to obtain a mutant strain 168S4. Compared with the recombinant strain 168S1, the ability of the mutant strain 168S4 to synthesize surfactin is increased from 0.4 g/L to 1.4 g/L.

Example 4 Construction of Strain B. subtilis 168S7

On the basis of the mutant strain 168S4 prepared in Example 3, dhb operon, pks operon and pps operon of the mutant strain 168S4 are simultaneously knocked out according to the same strategy as in Example 1, so as to obtain the strain 168S7. Compared with the mutant strain 168S4, the yield of surfactin of the strain 168S7 is increased from 1.4 g/L to 1.7 g/L.

Example 5 Construction of Strain B. subtilis 168S8

On the basis of the strain 168S7 prepared in Example 4, swrC is expressed in the strain 168S7 according to the same strategy as in Example 1, so as to obtain the strain 168S8. Compared with the strain 168S7, the yield of surfactin of the strain 168S8 is increased to 2.3 g/L from 1.7 g/L.

Example 6 Construction of Strain B. subtilis 168S11

On the basis of the strain 168S7 prepared in Example 4, swrC and acrB are simultaneously expressed in the strain 168S7 according to the same strategy as in Example 1, so as to obtain the strain 168S11. Compared with the strain 168S7, the yield of surfactin of the strain 168S11 is increased from 1.7 g/L to 2.9 g/L.

Example 7 Construction of Strain B. subtilis 168S12

On the basis of the strain 168S7 prepared in Example 4, swrC, acrB and lialHGFSR are simultaneously expressed in the strain 168S7 according to the same strategy as in Example 1, so as to obtain the strain 168S12. Compared with the strain 168S7, the yield of surfactin of the strain 168S12 is increased from 2.9 g/L to 3.8 g/L.

Example 8 Construction of Strain B. subtilis 168S13

On the basis of the strain 168S12 prepared in Example 7, fabHB is expressed in the strain 168S12 according to the same strategy as in Example 1, so as to obtain the strain 168S13. Compared with the strain 168S12, the yield of surfactin of the strain 168S13 is increased from 3.8 g/L to 4.9 g/L.

Example 9 Construction of Strain B. subtilis 168S15

On the basis of the strain 168S12 prepared in Example 7, IpdV, bkdAA, bkdAB, bkdB and lipALM are simultaneously expressed in the strain 168S12 according to the same strategy as in Example 1, so as to obtain the strain 168S15. Compared with the strain 168S12, the yield of surfactin of the strain 168S15 is increased from 3.8 g/L to 4.6 g/L.

Example 10 Construction of Strain B. subtilis 168S16

On the basis of the strain 168S12 prepared in Example 7, fabHB, IpdV, bkdAA, bkdAB, bkdB and lipALM are simultaneously expressed in the strain 168S12 according to the same strategy as in Example 1, so as to obtain the strain 168S16. Compared with the strain 168S12, the yield of surfactin of the strain 168S16 is increased from 3.8 g/L to 5.6 g/L.

Example 11 Construction of Strain B. subtilis 168S20

On the basis of the strain 168S12 prepared in Example 7, fabHB and fabD-accDABC are simultaneously expressed in the strain 168S12 according to the same strategy as in Example 1, so as to obtain the strain 168S20. Compared with the strain 168S12, the yield of surfactin of the strain 168S20 is increased from 3.8 g/L to 5.6 g/L.

Example 12 Construction of Strain B. subtilis 168S21

On the basis of the strain 168S12 prepared in Example 7, fabHB, fabD-accDABC and fabF-fabG-fabZ-fabI are simultaneously expressed in the strain 168S12 according to the same strategy as in Example 1, so as to obtain the strain 168S21. Compared with the strain 168S12, the yield of surfactin of the strain 168S21 is increased from 3.8 g/L to 4.7 g/L.

Example 13 Construction of Strain B. subtilis 168S22

On the basis of the strain 168S12 prepared in Example 7, fabHB, fabD-accDABC, fabF-fabG-fabZ-fabI and tesA are simultaneously expressed in the strain 168S12 according to the same strategy as in Example 1, so as to obtain the strain 168S22. Compared with the strain 168S12, the yield of surfactin of the strain 168S22 is increased to 7.3 g/L.

Example 14 Construction of Strain B. subtilis 168S23

On the basis of the strain 168S22 prepared in Example 14, IpdV, bkdAA, bkdAB, bkdB, lipALM, alsS ilvD, ilvC and leuABCD are expressed in the strain 168S22 according to the same strategy as in Example 1, so as to obtain the strain 168S23. Compared with the strain 168S22, the yield of surfactin of the strain 168S23 is increased from 7.3 g/L to 8.5 g/L.

Example 15 Construction of Strain B. subtilis 168S24

On the basis of the strain 168S23 prepared in Example 14, pfkA and pyk are expressed in the strain 168S23 according to the same strategy as in Example 1, so as to obtain the strain 168S24. Compared with the strain 168S23, the yield of surfactin of the strain 168S24 is increased from 8.5 g/L to 8.9 g/L.

Example 16 Construction of Strain B. subtilis 168S27

On the basis of the strain 168S24 prepared in Example 15, gap, pgk, pgm, eno and pdhABCD are expressed in the strain 168S24 according to the same strategy as in Example 1, so as to obtain the strain 168S27. Compared with the strain 168S24, the yield of surfactin of the strain 168S27 is increased from 8.9 g/L to 9.8 g/L.

Example 17 Construction of Strain B. subtilis 168S28

Based on the strain 168S27 prepared in Example 16, comQXPA of *B. amyloliquefaciens* MT45 and PsrfA of *B. amyloliquefaciens* MT45 are expressed in the strain 168S27 according to the same strategy as in Example 1, so as to obtain the strain 168S28. Compared with the strain 168S27, the yield of surfactin of the strain 168S28 is increased from 9.8 g/L to 11.5 g/L.

Example 18 Construction of Strain B. subtilis 168S35

Based on the strain 168S27 prepared in Example 17, according to the same strategy as in Example 1, comQXPA of *B. amyloliquefaciens* MT45 and PsrfA of *B. amyloliquefaciens* MT45 are expressed in the strain 168S27 and codY is knocked out to obtain the strain 168S35. Compared with the strain 168S27, the yield of surfactin of the strain 168S35 is increased from 9.8 g/L to 12.8 g/L.

Example 19 Construction of Strain B. subtilis 168S32

On the basis of the strain 168S27 prepared in Example 17, the spX gene of the strain 168S27 is knocked out according to the same strategy as in Example 1 to obtain the strain 168S32. Compared with the strain 168S27, the yield of surfactin of the strain 168S32 is increased from 9.8 g/L to 10.6 g/L,

Example 20 Construction of Strain B. subtilis 168S33

On the basis of the strain 168S27 prepared in Example 17, the perR gene of the strain 168S27 is knocked out according to the same strategy as in Example 1 to obtain the strain 168S33. Compared with the strain 168S27, the yield of surfactin of the strain 168S33 is increased from 9.8 g/L to 10.5 g/L.

---

What is claimed is:

1. A method of modifying *Bacillus subtilis* to enhance synthesis of surfactin, which comprises:
   replacing one or more of the *B. subtilis* sfp genes with one or more equivalent *Bacillus amyloliquefaciens* sfp genes; and
   performing a transformation of the *B. subtilis*, as follows:
      knocking out one or more:
         biofilm formation genes,
         non-ribosome peptide synthases/polyketide synthase (NRPS/PKS) gene clusters, or
         one or more -negative regulatory factors, and/or,
      overexpressing at least one of:
         one or more surfactin efflux and resistance genes,
         one or more branched chain fatty acid synthesis pathway genes,
         one or more glycolytic pathway genes, and
         an exogenous cluster effect system gene,
   wherein the biofilm formation genes comprise: epsA-O and tasA-sipW-yqxM;
   wherein the NRPS/PKS gene clusters comprises: a dhb operon expressing a siderophore bacillibactin synthase, a pks operon expressing a polyketide synthase, and a pps operon expressing a fengycin synthase;
   wherein the negative regulatory factors comprise one or more of: codY, rapCFH, sinI, spx, perR, and phoP;
   wherein the surfactin efflux and resistance genes comprise: swrC, liaRSFGHI, and acrB;
   wherein the branched chain fatty acid synthesis pathway genes comprise: fabHB, lpdV, bkdAA, bkdAB, bkdB, lipALM, alsS, ilvD, ilvC, leuABCD, fabD, accDABC, fabF, fabG, fabZ, fabI, and tesA;
   wherein the glycolytic pathway genes comprise: pfkA, gapA, pgk, and pdhABCD; and
   wherein the exogenous cluster effect system genes comprises comQXPA.

2. The method of claim 1, wherein the sfp genes of *B. subtilis* 168 are replaced with *B. amyloliquefaciens* MT45 sfp genes by homologous recombination.

3. The method of claim 1, which comprises knocking out at least two of:
   (i) the one or more biofilm formation genes,
   (ii) the NRPS/PKS gene clusters, and
   (iii) the one or more negative regulatory factors.

4. The method of claim 1, which comprises-over-expressing at least two of:
   (a) the surfactin efflux and resistance genes,
   (b) the branched chain fatty acid synthesis pathway genes, (c) the glycolytic pathway genes, and (d) exogenous cluster effect system genes.

5. The method of claim 1, wherein comQXPA and srfA promoters are combined for expression.

6. The method of claim 1, wherein the knockout is performed by homologous recombination, and wherein the length of a homologous arm of the homologous recombination is 1000 bp to 2000 bp.

7. The method of claim 1, which comprises:
   replacing the sfp genes in B. subtilis 168 with B. amyloliquefaciens MT45 sfp genes,
   knocking out epsA-O, tasA-sipW-yqxM, dhb operon, pks operon, pps operon, codY, rapCFH, sinI, spx, perR, and phoP genes, and
   overexpressing fabHB, lpdV, bkdAA, bkdAB, bkdB, lipALM, alsS, ilvD, ilvC, leuABCD, fabD, accDABC, fabF, fabG, fabZ, fabI, tesA, pfkA, gapA, pgk, pdhABCD, and comQXPA genes.

8. The method of claim 7, wherein the sfp gene is WP_088612131.1.

9. The method of claim 1, wherein said B. subtilis comprises B. subtilis 168, B. subtilis WB400, B. subtilis WB600, B. subtilis WB800, and/or B. subtilis WB800N.

10. A recombinant Bacillus subtilis, wherein the recombinant B. subtilis is prepared by the method of claim 1.

11. A method for synthesizing surfactin, which comprises: fermenting the B. subtilis of claim 1.

12. The method of claim 11, wherein fermenting comprises incubating the B. subtilis in a fermentation medium which comprises:
   60 to 65 g/L of sucrose,
   5 to 10 g/L of ammonium nitrate,
   3 to 5 g/L of peptone,
   2 to 5 g/L of potassium dihydrogen phosphate,
   8 to 12 g/L of disodium hydrogen phosphate,
   0.05 to 0.15 g/L of magnesium sulfate,
   5 to 8 µM of calcium chloride,
   2 to 5 µM of ferrous sulfate, and
   2 to 5 µM of ethylenediamine tetraacetic acid (EDTA).

* * * * *

SEQUENCE LISTING

```
<160> NUMBER OF SEQ ID NOS: 14

<210> SEQ ID NO 1
<211> LENGTH: 25
<212> TYPE: DNA
<213> ORGANISM: Artificial Sequence
<220> FEATURE:
<223> OTHER INFORMATION: Synthetic DNA

<400> SEQUENCE: 1
aattgttatt gattttatat gctgc                                          25

<210> SEQ ID NO 2
<211> LENGTH: 44
<212> TYPE: DNA
<213> ORGANISM: Artificial Sequence
<220> FEATURE:
<223> OTHER INFORMATION: Synthetic DNA

<400> SEQUENCE: 2
aatgtatgct atacgaacgg taatggaccg tctttctttt ctaa                     44

<210> SEQ ID NO 3
<211> LENGTH: 44
<212> TYPE: DNA
<213> ORGANISM: Artificial Sequence
<220> FEATURE:
<223> OTHER INFORMATION: Synthetic DNA

<400> SEQUENCE: 3
agcatacatt atacgaacgg tattattgat ttgccaaaat gaca                     44

<210> SEQ ID NO 4
<211> LENGTH: 25
<212> TYPE: DNA
```

```
<213> ORGANISM: Artificial Sequence
<220> FEATURE:
<223> OTHER INFORMATION: Synthetic DNA

<400> SEQUENCE: 4
aagtgctgga gccgggagaa gaaac                                      25

<210> SEQ ID NO 5
<211> LENGTH: 44
<212> TYPE: DNA
<213> ORGANISM: Artificial Sequence
<220> FEATURE:
<223> OTHER INFORMATION: Synthetic DNA

<400> SEQUENCE: 5
ttagaaaaga aagacggtcc attaccgttc gtatagcata catt                 44

<210> SEQ ID NO 6
<211> LENGTH: 44
<212> TYPE: DNA
<213> ORGANISM: Artificial Sequence
<220> FEATURE:
<223> OTHER INFORMATION: Synthetic DNA

<400> SEQUENCE: 6
tgtcattttg gcaaatcaat aataccgttc gtataatgta tgct                 44

<210> SEQ ID NO 7
<211> LENGTH: 25
<212> TYPE: DNA
<213> ORGANISM: Artificial Sequence
<220> FEATURE:
<223> OTHER INFORMATION: Synthetic DNA

<400> SEQUENCE: 7
atgaacaaac atgtaaataa agtag                                      25

<210> SEQ ID NO 8
<211> LENGTH: 40
<212> TYPE: DNA
<213> ORGANISM: Artificial Sequence
<220> FEATURE:
<223> OTHER INFORMATION: Synthetic DNA

<400> SEQUENCE: 8
tgtatgctat acgaacggta gaaacggaat ctcgcagaat                      40

<210> SEQ ID NO 9
<211> LENGTH: 40
<212> TYPE: DNA
<213> ORGANISM: Artificial Sequence
<220> FEATURE:
<223> OTHER INFORMATION: Synthetic DNA

<400> SEQUENCE: 9
catacattat acgaacggta cgccgaaatg cctccggttt                      40

<210> SEQ ID NO 10
<211> LENGTH: 42
<212> TYPE: DNA
<213> ORGANISM: Artificial Sequence
<220> FEATURE:
<223> OTHER INFORMATION: Synthetic DNA

<400> SEQUENCE: 10
aaacattgtt gaagttcatc atgtgtacat tcctctctta cc                   42
```

```
<210> SEQ ID NO 11
<211> LENGTH: 42
<212> TYPE: DNA
<213> ORGANISM: Artificial Sequence
<220> FEATURE:
<223> OTHER INFORMATION: Synthetic DNA

<400> SEQUENCE: 11
ggtaagagag gaatgtacac atgatgaact tcaacaatgt tt                             42

<210> SEQ ID NO 12
<211> LENGTH: 42
<212> TYPE: DNA
<213> ORGANISM: Artificial Sequence
<220> FEATURE:
<223> OTHER INFORMATION: Synthetic DNA

<400> SEQUENCE: 12
ccaaacagga agctctgtgt cttatgagtc atgatttact aa                             42

<210> SEQ ID NO 13
<211> LENGTH: 42
<212> TYPE: DNA
<213> ORGANISM: Artificial Sequence
<220> FEATURE:
<223> OTHER INFORMATION: Synthetic DNA

<400> SEQUENCE: 13
ttagtaaatc atgactcata agacacagag cttcctgttt gg                             42

<210> SEQ ID NO 14
<211> LENGTH: 24
<212> TYPE: DNA
<213> ORGANISM: Artificial Sequence
<220> FEATURE:
<223> OTHER INFORMATION: Synthetic DNA

<400> SEQUENCE: 14
gttgcggtta gttgactttt tgtt                                                 24
```